(12) United States Patent
Pettersson et al.

(10) Patent No.: US 10,105,468 B2
(45) Date of Patent: *Oct. 23, 2018

(54) IMPLANTS WITH WEAR RESISTANT COATINGS AND METHODS

(71) Applicant: IHI Ionbond AG, Olten (CH)

(72) Inventors: Maria Pettersson, Uppsala (SE);
Håkan Engqvist, Östhammar (SE);
Johanna André, Uppsala (SE); Lars Hultman, Linköping (SE)

(73) Assignee: IHI Ionbond AG (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/810,243

(22) Filed: Nov. 13, 2017

(65) Prior Publication Data

US 2018/0064847 A1    Mar. 8, 2018

Related U.S. Application Data

(60) Division of application No. 15/183,080, filed on Jun. 15, 2016, now Pat. No. 9,833,545, which is a
(Continued)

(30) Foreign Application Priority Data

May 8, 2012   (SE) ..................... 1200277

(51) Int. Cl.
*A61F 2/28*     (2006.01)
*A61F 2/30*     (2006.01)
(Continued)

(52) U.S. Cl.
CPC .......... *A61L 27/306* (2013.01); *A61F 2/3094* (2013.01); *A61F 2/30767* (2013.01);
(Continued)

(58) Field of Classification Search
None
See application file for complete search history.

(56) References Cited

U.S. PATENT DOCUMENTS 4,608,051 A   8/1986  Reck et al.
6,534,197 B2  3/2003  Noda et al.
(Continued)

FOREIGN PATENT DOCUMENTS

EP    1923079 A1    5/2008
EP    1992309 A1    11/2008
(Continued)

OTHER PUBLICATIONS

Ehiasarian, Arutium P., "High-Power Impulse Magnetron Sputtering and Its Applications," Pure Appl Chem vol. 82, No. 6, pp. 1247-1258; 2010.
(Continued)

*Primary Examiner* — David H Willse
*Assistant Examiner* — Javier Blanco
(74) *Attorney, Agent, or Firm* — Dinsmore & Shohl LLP

(57) ABSTRACT

An implant comprises a substrate and a coating on a surface of the substrate, and the coating includes silicon nitride and has a thickness of from about 1 to about 15 micrometer wherein the silicon nitride coating has a composition defined by $Si_xN_yW_z$, where W is C, H and/or O, $2<x<4$, $3<y<5$, and z is such that the coating contains less than 20 atomic percent of C, H and O.

9 Claims, 9 Drawing Sheets

Related U.S. Application Data continuation of application No. 14/239,384, filed as application No. PCT/IB2012/054471 on Aug. 30, 2012, now Pat. No. 9,393,348.

(60) Provisional application No. 61/528,899, filed on Aug. 30, 2011.

(51) Int. Cl.

| | | |
|---|---|---|
| *A61F 2/32* | (2006.01) | |
| *A61F 2/34* | (2006.01) | |
| *A61F 2/36* | (2006.01) | |
| *A61F 2/38* | (2006.01) | |
| *A61F 2/40* | (2006.01) | |
| *A61L 27/30* | (2006.01) | |
| *A61L 27/04* | (2006.01) | |
| *A61L 27/06* | (2006.01) | |
| *A61L 27/10* | (2006.01) | |
| *A61L 27/16* | (2006.01) | |
| *A61L 31/02* | (2006.01) | |
| *A61L 31/04* | (2006.01) | |
| *A61L 31/08* | (2006.01) | |
| *A61L 27/50* | (2006.01) | |
| *A61L 27/28* | (2006.01) | |

(52) U.S. Cl.
CPC .......... *A61L 27/042* (2013.01); *A61L 27/045* (2013.01); *A61L 27/06* (2013.01); *A61L 27/10* (2013.01); *A61L 27/16* (2013.01); *A61L 27/303* (2013.01); *A61L 27/50* (2013.01); *A61L 31/022* (2013.01); *A61L 31/026* (2013.01); *A61L 31/048* (2013.01); *A61L 31/084* (2013.01); *A61L 31/088* (2013.01); *H05K 999/99* (2013.01); *A61F 2002/3098* (2013.01); *A61F 2310/00317* (2013.01); *A61F 2310/00874* (2013.01); *A61L 27/28* (2013.01); *A61L 2400/10* (2013.01); *A61L 2400/12* (2013.01); *A61L 2420/02* (2013.01); *A61L 2420/08* (2013.01); *A61L 2430/12* (2013.01); *A61L 2430/24* (2013.01)

(56) References Cited

U.S. PATENT DOCUMENTS

| | | |
|---|---|---|
| 9,060,864 B1 | 6/2015 | Hofmann |
| 2006/0251875 A1 | 11/2006 | Carlisle et al. |
| 2008/0221683 A1 | 9/2008 | Deutchman et al. |
| 2008/0255674 A1 | 10/2008 | Rahaman et al. |
| 2010/0016987 A1 | 1/2010 | Scrafton et al. |
| 2010/0047434 A1 | 2/2010 | Kumar |

FOREIGN PATENT DOCUMENTS

| | | |
|---|---|---|
| JP | 62-22071 | 9/1987 |
| JP | 2005281779 A | 10/2005 |
| JP | 2006122435 A | 5/2006 |
| WO | 2009095705 | 8/2009 |
| WO | 2013030787 A1 | 3/2013 |

OTHER PUBLICATIONS

Nishiyama, Katsuhiro et al, "Friction and Wear of SIC, SI3N4, B4C—TiB2 and Al2O3"; Faculty of Science and Technology, Science University of Tokyo, 2641 Yamazaki, Noda 278; Aug. 31, 1992; Powder and Powder Metallurgy 1993.

IMPLANTS WITH WEAR RESISTANT COATINGS AND METHODS

CROSS-REFERENCE TO RELATED APPLICATIONS

This application is a divisional of U.S. patent application Ser. No. 15/183,080 filed Jun. 15, 2016, which is a continuation of U.S. patent application Ser. No. 14/239,384 filed Jun. 3, 2014 (now U.S. Pat. No. 9,393,348), which is the U.S. National Phase of PCT/IB2012/054471 filed Aug. 30, 2012, which claims priority of U.S. Provisional Patent Application 61/528,899 filed Aug. 30, 2011, and Swedish Patent Application 1200277-0 filed May 8, 2012.

FIELD OF THE INVENTION

The present invention relates to wear resistant implants, and in particular implants including a wear resistant coating. The present invention also relates to methods of producing such implants.

BACKGROUND OF THE INVENTION

Joint replacement is one of the most commonly performed orthopaedic operations. A total joint replacement has an average life span of about 15 years. The reason for implant failure may be due to one or more of several factors, but often is caused by wear particles from the bearing surface of the implant. Wear particles from implants have been linked to inflammation which lead to bone loss and, eventually, implant loosening, Sargeant et al, "Hip Implants: Paper V. Physiological Effects", *Materials & Design*, 27 (2006) 287-307. The chemistry and particle size of such particles have been found to be of high importance to the inflammation response, Sargeant et al (2006) and Sargeant et al, "Hip Implants—Paper VI—Ion Concentrations", Materials & Design 28 (2007) 155-171.

Cobalt chromium (CoCr) based metals are commonly used as biomaterial for implants and have been shown to be relatively good, biocompatible materials for joint applications. Their mechanical properties are adequate for use as load-bearing joint implants. However, experiments have shown that CoCr particles released from implants due to wear and corrosion can restrain bone growth, Aspenberg et al, "Benign response to particles of diamond and SiC: bone chamber studies of new joint replacement coating materials in rabbits", *Biomaterials,* 17 (1996) 807-812. Titanium alloys and stainless steels have also been used frequently in joint implants, Sargeant et al (2006). The main risks with metal alloy implants are release of metal ions due to corrosion and wear, and these metal ions can be carcinogenic. The wear particles may also lead to bone resorption, Sargeant et al (2007).

Use of a liner of ultra high molecular weight polyethylene (UHMWPE) against a metal or ceramic head, having a relatively low measured coefficient of friction, has been proposed, but the UHMWPE liner often gets worn and produces a relatively large amount of wear particles that can cause aseptic loosening, Xiong et al, "Friction and wear properties of UHMWPE/$Al_2O_3$ ceramic under different lubricating conditions", Wear, 250 (2001) 242-245.

Alumina ($Al_2O_3$) and zirconia ($ZrO_2$) ceramics have been used in joint replacements to provide high wear resistance and chemical inertness. However, ceramic materials have a poor tensile strength and alumina components in joint replacements have been shown to release wear particles due to low toughness. The particles released from alumina and zirconia are also inert and will not be resorbed by the body. However, there are other ceramic materials that have shown promising results. For example, silicon nitride ($Si_3N_4$) has a higher fracture toughness and is more resistant to microcrack propagation than alumina, Bal et al, "Fabrication and Testing of Silicon Nitride Bearings in Total Hip Arthroplasty: Winner of the 2007 'HAP' PAUL Award", *The Journal of Arthroplasty,* 24 (2009) 110-116.

One solution to the problems related to bulk metal joint implants or ceramic joint implants is to coat a metal joint with a more wear resistant, low corrosion ceramic coating, for example, a titanium nitride coating. However, the problems of inert wear particles causing long term problems such as inflammation and aseptic loosening have not been resolved.

Accordingly, a need exists for wear and corrosion resistant biomedical implants, especially for use as artificial joints, to overcome the problems of wear particle formation and assorted high inflammation.

SUMMARY OF THE INVENTION

Accordingly, it is an object of the invention to provide implants and methods which overcome various disadvantages of the prior art.

In one embodiment, the invention is directed to an implant comprising a substrate and a coating on a surface of the substrate, the coating comprising silicon nitride and having a thickness of from about 1 to about 15 micrometer.

In another embodiment, the invention is directed to a method of providing an implant which comprises coating a surface of an implant substrate with a coating comprising silicon nitride and having a thickness of from about 1 to about 15 micrometer by physical vapour deposition.

The implants and methods of the invention are advantageous in providing implants with a combination of properties suitable for use in vivo while also exhibiting improved wear resistance and, particularly, reduced tendency to release wear particles causing inflammation and implant loosening. Particularly, particles released by the present implants are resorbable and reduce the possibility of inflammation and implant loosening resulting from wear particles.

These and additional advantages, objects and embodiments of the invention will be more fully apparent in view of the following detailed description.

BRIEF DESCRIPTION OF THE DRAWINGS

The detailed description will be more fully understood in view of the drawings, in which:

FIG. 2A shows selected area electron diffraction (SAED), which corresponds to $Si_3N_4$; FIG. 2B shows a high resolution TEM (HRTEM) image of an $Si_3N_4$ lattice within the coating.

FIG. 3A is Coating no. 5 on Si-substrate; FIG. 3B is Coating no. 2 on CoCr substrate.

FIG. 4A shows Coating no. 3 with a fine columnar structure; FIG. 4B shows Coating no. 5 with a columnar structure; FIG. 4C shows Coating no. 8 with a columnar structure; FIG. 4D shows Coating no. 10 without a distinct columnar structure.

Figure 1:
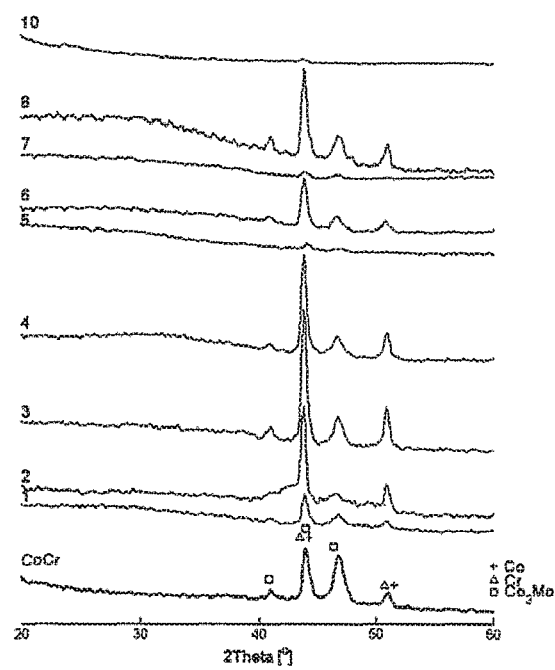
FIG. 1 shows X-ray diffraction (XRD) patterns of $Si_xN_y$-coatings on CoCr substrates and of CoCr substrates, as described in Example 1.

The Drawings are non-limiting of the invention defined in the claims.

DETAILED DESCRIPTION

The present invention relates to implants comprising a substrate and a coating. The coating is wear resistant with high mechanical strength and forms resorbable wear particles. The invention also relates to methods of providing wear resistant biomedical implants.

The implant substrate may be any desired implant material. In specific embodiments, the substrate may be ceramic or metallic. Suitable metals can be found in the group of cobalt-chromium alloys, stainless steel alloys, titanium and titanium alloys. In another embodiment, the substrate may be formed of ultra high molecular weight polyethylene (UHMWPE). Combinations of two or more of these materials may also be employed. In a more specific embodiment, the substrate is a Cobalt-Chromium alloy. The substrate may be cleaned and/or polished to a very fine surface finish prior to coating. In one embodiment, the substrate is polished to provide a surface finish of below (Ra) 10 nm in surface roughness prior to receiving the wear resistant coating according to the present invention, as a rough substrate typically increases the generation of wear particles as compared with a smooth surface and, conversely, a smooth surface will reduce the tendency to generate wear particles. Within the present disclosure, surface roughness is measured with an optical profiler in PSI (phase-shifting interferometry) mode over an area of ~400×500 μm, using a ×10 lens and FOV 1 in a Wyko, NT-110 Veeco, as described by Kim, "Surface Roughness of Ceramic Femoral Heads after In-Vivo Transfer of Metal Correlation to Polyethylene Wear", *Bioceramics and Alternative Bearings in Joint Arthroplasty*, J.-D. Chang, K. Billau (Eds.), Steinkopff (Pub.), 2007, pp. 49-57.

The coating material is based on silicon nitride and the coating has a thickness of from about 1 to about 15 micrometer. In a specific embodiment, the coating has a thickness of from about 1 to about 10 micrometer. Above about 15 micrometer, the coating adhesion is too weak, while below about 1 micrometer, the coating life time is too short. As discussed in further detail below, the coating is formed using a physical vapour deposition (PVD) method. In specific embodiments, the hardness of the coating ranges between 5-45 GPa, or, more specifically, from about 15 to 45 GPa, measured with a commercial nanoindenter (CSM Instruments UNHT) with a Berkovich tip, using the Oliver-Pharr method (Oliver et al, An improved technique for determining hardness and elastic modulus using load and displacement sensing indentation experiments, *Journal of Materials Research*, 7 (1992) 1564-1583). Measurement of elastic modulus is also made using the Oliver-Pharr method.

In specific embodiments, the coating as deposited has a surface roughness of less than about 50 nm, more specifically less than about 20 nm. In further specific embodiments, the coating can be polished to a fine surface roughness below about 10 nm in roughness, using methods known in the art. In additional specific embodiments, the coatings have a coefficient of friction less than about 0.5, more specifically, less than about 0.3, or, more specifically, less than about 0.25. In further embodiments, the coating has a wear resistance after 10,000 revolutions in bovine serum solution of less than about $10\times10^{-7}$ mm$^3$/Nm, measured according to the technique as described in Example 1.

The coating can be single layered, multilayered and/or of compositional gradient structure, and may optionally be provided with an adhesion layer if desired. The coating may be crystalline, nanocrystalline or amorphous, or a combination of crystalline, nanocrystalline and amorphous. The coating can also comprise crystals embedded into an amorphous phase. In specific embodiments, the coating comprises $Si_3N_4$, or is of the formula $Si_xN_y$, where 2<x<4 and 3<y<5, and may be either of α-phase, β-phase, gamma phase or amorphous phase, or combinations thereof. A typical average grain size in the coating is below 1 micrometer, or more specifically, below 500 nm, to provide a high strength coating. In more specific embodiments, the average grain size is larger then about 1 nm.

The coating may also comprise additions of C, H, O or combinations thereof. In specific embodiments, the substitutions are individually below 20 atomic %, and, in a more specific embodiment, are combined less than 20 atomic %. Thus, in specific embodiments, the silicon nitride coating has a composition of $Si_xN_yW_z$, where W is C, H and/or O, and $2<x<4$ and $3<y<5$ and z is such that the material contains less than 20 atomic percent of C, H and O. For very high degrees of substitution the lattice structure is not stable and other less wear resistant or non-resorbable phases will form.

When wear particles are released from the coating, the wear particles are small, in certain embodiments, below 1 micrometer, and in further embodiments, below 100 nanometer. Such particles hence have a large surface area compared to their volume, which increases the dissolution rate for the particles in body fluid.

The coating as described is preferably formed by PVD, and in a specific embodiment, is deposited using reactive sputtering, where nitrogen gas ($N_2$) is let in to the chamber and reacts with the sputtered molecules (here, predominately Si) from a target (a silicon-containing material). Suitable flow rates of $N_2$ and argon (Ar) are shown in Table 1. Also, other gases can be provided to the chamber for reaction with the sputtered atoms. For example, ethylene, $C_2H_4$, which results in a coating containing carbon and hydrogen, can be provided to the chamber. A preferred flow rate of $C_2H_4$, if employed, is shown in Table 1. The target is suitably silicon. Additional exemplary targets include, but are not limited to, silicon carbide and silicon nitride. The power of the target is suitably from 150 W and higher. In specific embodiments, the sputtering process is performed using radio frequency sputtering, for example, with a frequency of above 10 kHz, more specifically, 13.56 kHz.

In a more specific embodiment, the coatings according to the present invention are deposited using high-power pulsed magnetron sputtering (HiPIMS). The coatings can then be deposited using a silicon target in a Ar/$N_2$ atmosphere. Extra carbon may optionally be obtained in the coatings using a carbon target, or from a gas/liquid containing carbon, for example, $C_2H_4$. The samples can be rotated in the chamber to obtain depositions of both the silicon and the carbon target. Deposition parameters, such as target power and temperature in the chamber, may be varied to form different microstructures and compositions, as demonstrated in the Examples. See Table 3. Suitable parameters for additional embodiments of the deposition of the coatings are also indicated in Table 4.

The substrate temperature during the coating process may be varied as desired. In specific embodiments, the temperature is from about 100° C. to 600° C., more specifically, from about 200 to 400° C. The chamber pressure during the coating process may be varied as desired. In specific embodiments, the chamber pressure is normally from about $0.5 \cdot 10^{-6}$ to $2 \cdot 10^{-5}$ bar. In specific embodiments, the working gas is normally argon gas.

The aforementioned additives (C, H, O) and/or the deposition process may be may be used to control the hardness, elastic modulus, wear resistance, solubility, surface energy and/or chemical affinity, for example, the retention of synovial fluid on the coating surface in vivo, of the coating. Thus, the additives and/or the deposition process can influence the functionality of the coating. A higher solubility of the coating provides a faster resorption of wear particles when formed in vivo. The solubility is, in one embodiment, controlled via solid-state substitutions in the silicon nitride lattice. Generally, for $Si_xN_y$ coatings, a higher hardness and a higher elastic modulus are obtained when the coating is applied with lower Si-target power, for example, in the range of 1 kW to 4 kW. Generally, for $Si_xN_yC_z$ coatings, a lower surface roughness is obtained when the coating is applied with lower Si-target power, for example, in the range of 1 kW to 4 kW. Additionally, the composition may be varied to obtain a desired crystalline structure. For example, dense microstructures having a higher wear resistance may be obtained with $Si_xN_y$ coatings, while columnar and laminar structures may be obtained with $Si_xN_yC_z$ coatings.

The implants may be of any desired physical form for use in various body locations, and a portion or the entirety of the substrate may be coated with the coating according to the invention. For joint implants, the head or the cup can be coated but it is preferable that both components are coated with the silicon nitride-based coating. Both components can have the same type of substrate, e.g. cobalt chromium-cobalt chromium, or may be of different materials. Also, in modular hip joints, both the male and female parts may be coated to reduce the wear. For knee joint implants, either just the femoral or the tibial component, or both components, are coated with the silicon nitride-based coating as described herein. For elbow joint implants, either just the bearing parts of the ulnar component, the humeral component, the bearing and the hinge pin, or all of these parts can be coated. Also, components for other joints, including, but not limited to, the shoulder, wrist, angle, fingers and toes, orthopaedic and dental screws, needles and plates, can be provided with the silicon nitride-based coating as described herein.

EXAMPLES

The following Examples demonstrate various embodiments of the invention, providing silicon nitride coatings on CoCr substrates, and testing various properties of the implants.

Example 1

$Si_xN_y$-coatings were deposited on CoCr substrates of type ASTM F1537 and also on silicon wafer substrates. First, the substrates were polished to a surface roughness (Ra) of about 8 nm. Prior to deposition, the substrates were ultrasonically cleaned in acetone and ethanol for 5 min each. The coatings were deposited using reactive RF sputtering (13.56 kHz) utilising a silicon target with Ar/$N_2$ plasma atmosphere. Several process parameters were varied in order to optimise the coating composition and microstructure, see Table 1. For two of the coatings ethylene ($C_2H_4$) gas was introduced into the chamber as a reactive agent in order to dope the coatings with C. All substrates were heated during deposition, except for coating No. 2. To avoid overheating of the target, the coating process alternated between 10 min sputtering, and a 3 min break, for a total sputtering duration of 2 hours, except coating No. 3 which had a coating duration of 3 hours. The parameters for coating No. 1 were the start parameters and the parameters for the other coatings were varied from that combination.

TABLE 1

Parameters during coating processes.

| Coating No. | Substrate | | Ar (sccm) | $N_2$ (sccm) | Pressure (Pa) | T (° C.) | $C_2H_4$ (partial pressure, Pa) | Target Power (W) |
|---|---|---|---|---|---|---|---|---|
| 1 | — | CoCr | 10 | 30 | 1.0 | 280 | 0 | 300 |
| 2 | Si | CoCr | 10 | 30 | 1.0 | 25 | 0 | 300 |
| 3 | Si | CoCr | 10 | 30 | 1.0 | 280 | 0 | 150 |
| 4 | Si | CoCr | 10 | 30 | 0.5 | 280 | 0 | 300 |
| 5 | Si | CoCr | 10 | 30 | 1.5 | 280 | 0 | 300 |
| 6 | — | CoCr | 30 | 15 | 1.0 | 280 | 0 | 300 |

TABLE 1-continued

Parameters during coating processes.

| Coating No. | Substrate | Ar (sccm) | N$_2$ (sccm) | Pressure (Pa) | T (° C.) | C$_2$H$_4$ (partial pressure, Pa) | Target Power (W) |
|---|---|---|---|---|---|---|---|
| 7 | — CoCr | 20 | 20 | 1.0 | 280 | 0 | 300 |
| 8 | Si CoCr | 20 | 20 | 1.5 | 280 | 0 | 300 |
| 9 | Si — | 20 | 20 | 0.5 | 280 | 0 | 300 |
| 10 | Si CoCr | 10 | 30 | 1.3 | 280 | 9 · 10$^{-4}$ | 300 |
| 11 | Si CoCr | 10 | 30 | 1.3 | 280 | 1.5 · 10$^{-4}$ | 300 |

The coatings were evaluated with nano-hardness measurements. It was revealed that the coating hardness was approximately 22 GPa, which is about the same as for bulk Si$_3$N$_4$.

Coating Analysis

EDS (Energy Dispersive Spectroscopy) analysis revealed that the coatings contained about 3-5% C, 54-60% N and 36-41% Si, based on atomic %, and the individual composition for each coating can be seen in Table 2. It should be noted that there is a general error when determining compositions using EDS of about ±2 atomic %, this should be added to limits above.

No crystalline structure in the coatings was detected in x-ray diffraction (XRD), see FIG. 1. The only observed crystalline reflections could be indexed to Co, Cr and Co$_3$Mo, using International Centre for Diffraction Data, Reference files: Cobalt PDF no. 15-0806, Chromium PDF no. 88-2323, and Cobalt Molybdenum PDF no. 29-0488. But a distinguished amorphous bump in the diffraction from the coating (especially for No. 8) at 20-35°, was observed, see FIG. 1.

Figure 2A:
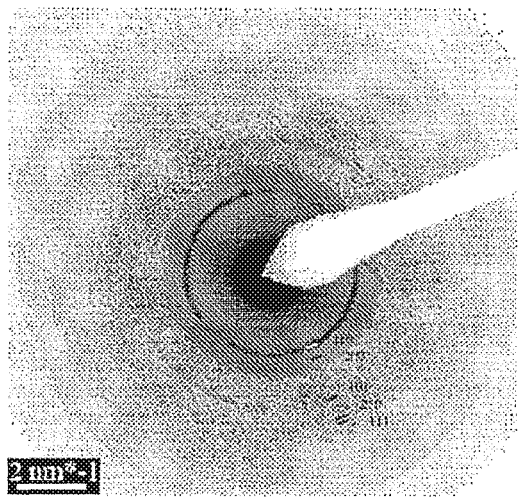
FIGS. 2A and 2B show transmission electron microscopy (TEM) images of coating No. 8, as described in Example 1.
Figure 2B:
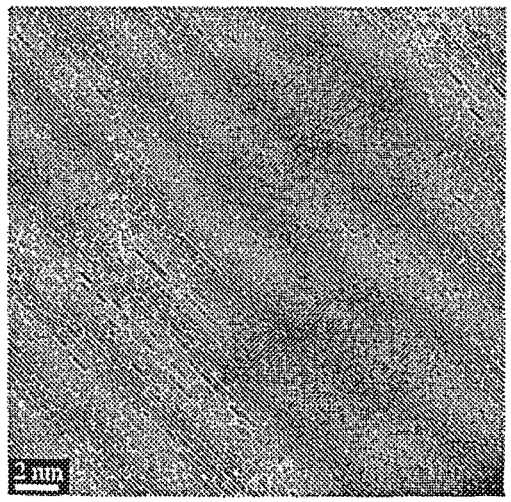

Selected area electron diffraction (SAED) of coating No. 8 using transmission electron microscopy (TEM) produced ring-like patterns with sharp dark speckles, representing a nanocrystalline structure, FIG. 2A. Via indexing the electron diffraction pattern, it was evident that all rings represented Si$_3$N$_4$. Furthermore, high resolution TEM (HRTEM) images exhibit lattice fringes consistent with a polycrystalline material, FIG. 2B. This means that the coatings are nanocrystalline and amorphous.

Figure 3A:
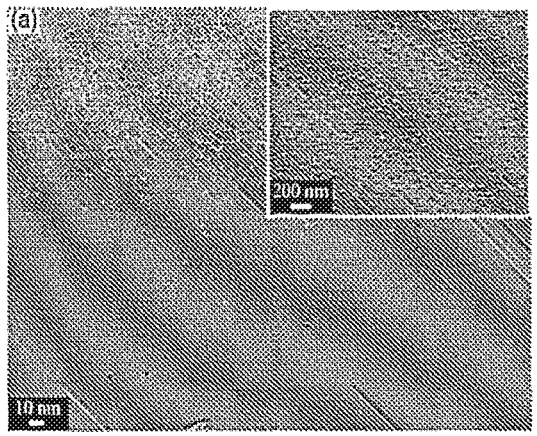
FIGS. 3A and 3B show the surface appearance of coatings at two magnifications, using scanning electron microscopy (SEM), 67° sample tilt, as described in Example 1.
Figure 3B:
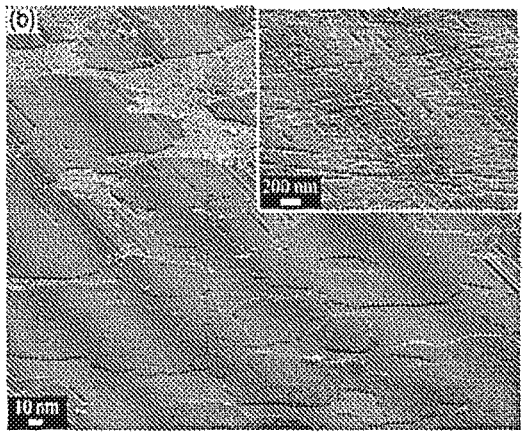
Figure 4A:
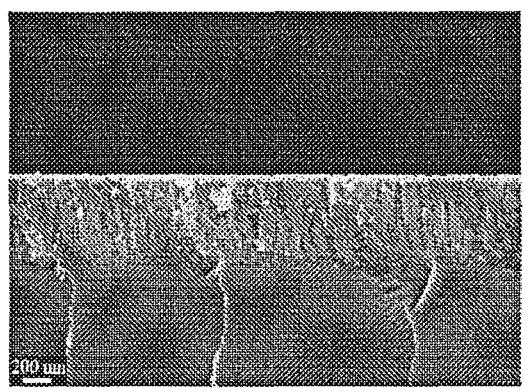
FIGS. 4A-4D show SEM images of cross sections of coatings on silicon wafer showing the resulting coating micro structure, as described in Example 1.
Figure 4B:
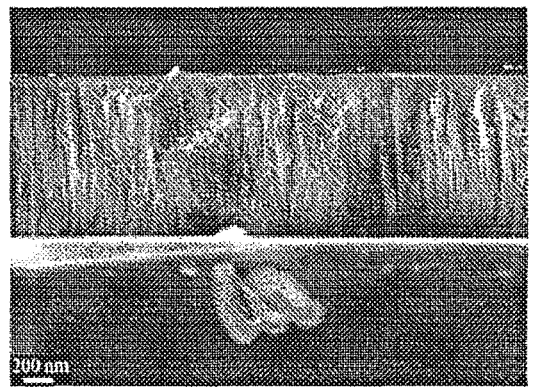
Figure 4C:
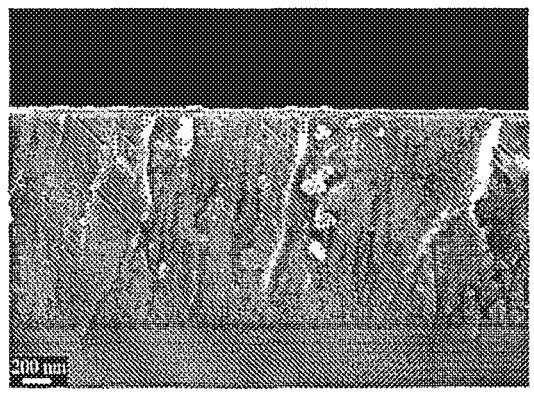
Figure 4D:
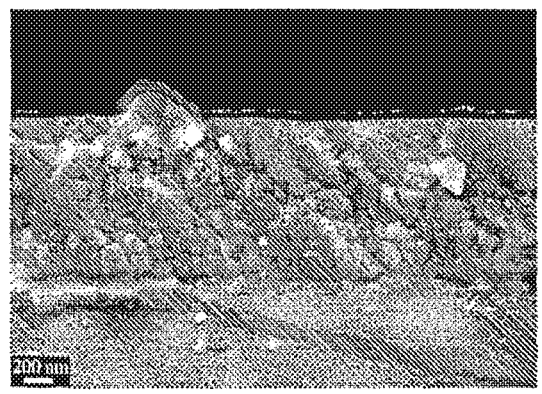

Almost all the Si$_x$N$_y$-coatings exhibited a fine surface nanostructure, as exemplified in, FIG. 3A. The only exception was coating No. 2 (deposited with a lower substrate temperature) which showed thin coating patches, FIG. 3B. The surface roughness (Ra) of coating No. 2 is too high, about 250 nm, while for the other coatings it is about 5 nm on Si substrates and 10 nm on CoCr substrates. This corresponds to a Ra of about 3 and 8 nm for the Si and CoCr substrates, respectively, prior to the coating deposition.

The images of cross sections of the coatings show that the character of the coating structure differs, as shown in FIGS. 4A-4D. Coatings Nos. 5 and 8 (FIGS. 4B and 4C) have a columnar structure and a thickness of approximately 1.4 µm. Coating No. 3, FIG. 4A (lower power supplied to target) has a similar structure to coatings Nos. 5 and 8, but with finer columns and the coating thickness is just approximately 600 nm. Coating No. 10, FIG. 4D (deposited with C$_2$H$_4$), is approximately 1.2 µm thick, has a much coarser microstructure than coatings Nos. 3, 5 and 8, but not as distinct columnar structure. Each coating, except coating No. 3 had a thickness of 1.2-1.8 µm, however that variation could be within one sample as well, due to the decreasing deposition rate from the centre below the target.

Friction and Wear Test

The coatings were tribologically tested using a ball-on-disc apparatus, where the coated discs were slid against a stationary polished ball of Si$_3$N$_4$ (6 mm in diameter, Spekuma, Sweden, representing a coated counter surface) while the coefficient of friction was continuously measured. The procedure was conducted in a similar manner as ASTM F 732-00 (Standard Test Method for Wear Testing of Polymeric Materials Used in Total Joint Prostheses, ASTM International, 2006). Under the ball, the tested material was rotated, forming a wear track of 5 mm in diameter at a speed of 0.04 m/s and normal load 1 N at room temperature. The wear test was run in a serum solution of 25% fetal bovine serum (Gibco) with sodium azide and ethylene-diaminetetraacetic acid (EDTA) according to ASTM F 732-00. The wear rate is quantified with a specific wear rate according to $$\text{Specific wear rate} = \frac{\text{Wear volume}}{\text{Load Sliding Distance}}. \quad \text{(Eq 1)}$$

Figure 5:
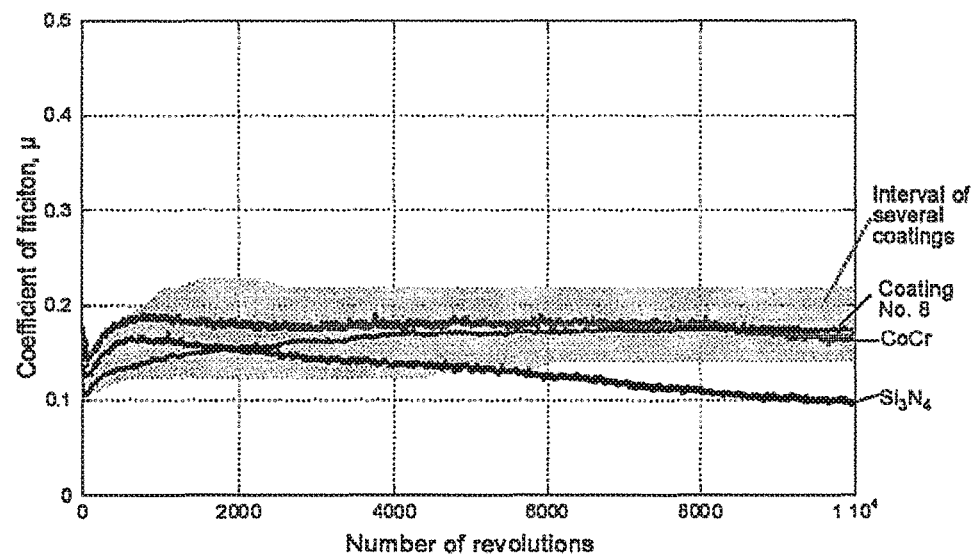
FIG. 5 shows the coefficient of friction versus number of revolutions for $Si_xN_y$-coatings, bulk CoCr and bulk $Si_3N_4$, as described in Example 1. The gray area represents the region in which almost all the coating curves are within, except coating no. 2 and 5 (not shown in the graph).

The wear rate, excluding the ball, was calculated from the worn cross-sectional area, measured with vertical scanning interferometry (VSI, Wyko NT-110). The friction measurements revealed no distinct difference in coefficient of friction between the different types of coatings, and bulk CoCr, FIG. 5. The major part of the coatings had a coefficient of friction between 0.12 and 0.22, indicated by the grey area in FIGS. 4A-4D. Almost all tests started with relatively fast and short friction decrease and then a longer increase of the coefficient of friction to then stabilise after about 2000 revolutions. However, coating No. 2 (deposited with a lower substrate temperature) had a coefficient of friction at 0.3, much higher than the rest of the coatings.

Figure 6:
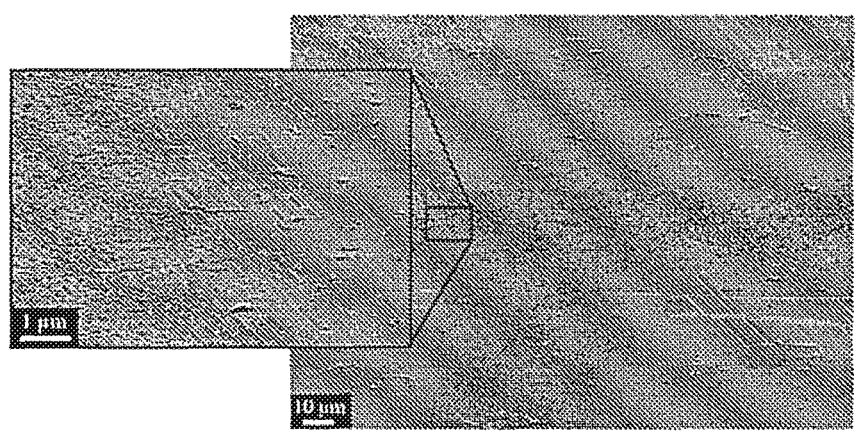
FIG. 6 is an SEM image of surface appearance of the wear-tracks on coating no. 8 after 10,000 revolutions at two different magnifications, 67° sample tilt, as described in Example 1. The coating is smoothed out in the wear-track.

The low wear rate of the coating demonstrates the potential of these coatings for use on bearing surfaces of joints. The coating topography was gradually smoothed out during sliding against the Si$_3$N$_4$-ball, in bovine serum solution, like coating No. 8, FIG. 6.

Figure 7:
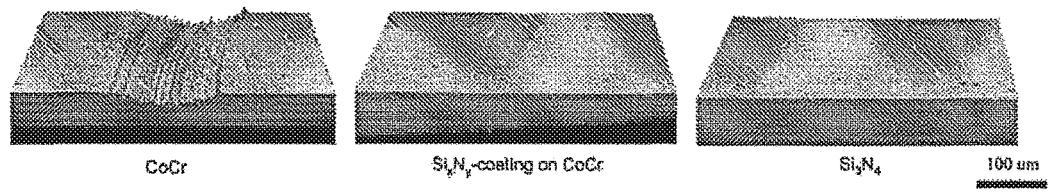
FIG. 7 shows optical profile images of worn surfaces and the calculated cross-sectional areas of the wear-tracks. The z-scale is magnified 23 times more than the x,y-scale.

The specific wear rate of the coatings after 10,000 revolutions was about 3×10$^{-7}$ mm$^3$/Nm, FIG. 7. In this image, where the z-scale has a higher magnification, grooves along the wear-track are visible in the coating wear-track as well. The wear amount of the coatings was similar to bulk Si$_3$N$_4$ which had a specific wear rate about 1×10$^{-7}$ mm$^3$/Nm. For CoCr, the specific wear rate was much higher, about 60×10$^{-7}$ mm$^3$/Nm.

Hardness

Hardness of the coatings was obtained with a commercial nanoindenter (CSM Instruments UNHT) with a Berkovich tip. A total of 30 indents per sample were completed with a maximum depth of 50 nm. Hardness and elastic modulus were determined with the Oliver-Pharr method.

Summary of the Coating Properties

Despite the variation of several deposition parameters, not much difference in the chemical composition, phase composition, nanostructure, tribological properties or hardness, see Table 2.

TABLE 2

Coating properties as well as atomic composition for some of the tested coatings.

| Coating | μ (coefficient of friction) | Atomic ratio (%) C | Atomic ratio (%) Si | Atomic ratio (%) N | Specific wear rate (mm³/Nm) | Mean hardness (GPa) |
|---|---|---|---|---|---|---|
| 1 | 0.15 | 5 | 40 | 54 | $3.0 \cdot 10^{-7}$ | 21.5 ± 2.7 |
| 2** | 0.3 | 4 | 36 | 60 | * | 24.2 ± 3.0 |
| 3 | 0.2 | 4 | 41 | 55 | $2.7 \cdot 10^{-7}$ | 21.2 ± 2.0 |
| 4 | 0.15 | 4 | 40 | 56 | $3.2 \cdot 10^{-7}$ | 22.3 ± 2.5 |
| 8 | 0.15 | 3 | 39 | 58 | $3.2 \cdot 10^{-7}$ | 18.0 ± 2.2 |
| 10 | 0.15 | 5 | 39 | 56 | $3.0 \cdot 10^{-7}$ | 21.6 ± 3.7 |

* The coating roughness was higher than the wear scar
** The coating was deposited at lower temperature Example 2

$Si_xN_y$- and $Si_xN_yC_z$-coatings were deposited on silicon wafers (001) with high-power pulsed magnetron sputtering system (HiPIMS, CemeCon CC800/9, Germany). The vacuum chamber (85×85×100 cm) of the industrial-scaled deposition system is equipped with four rectangular magnetron sputtering cathodes (50×8.8 cm) facing a table holder in the center. Unipolar pulses were applied to the magnetrons by a pulsing unit (SINEX 3, Chemfilt Ionsputtering AB, Sweden) charged by a direct current (DC) power supply (Pinnacle, Advanced Energy). The depositions were made with a silicon target with Ar/$N_2$ atmosphere. A Si-target (purity 99.999%) was used for all depositions. Extra carbon is obtained on a number of coatings (Nos. 18 to 28) with a carbon target (purity 99.5%). The samples are then rotated in the chamber to get depositions of both the silicon and the carbon target at a distance of 7.5 cm from the targets. For SiN coatings, the substrate was static perpendicular to the Si-target, and for SiCN coatings, the substrates where rotated. Deposition parameters, such as target power and temperature in the chamber, were varied to form different microstructures and compositions, see Table 3. The constant parameters during deposition can be seen in Table 4. Substrates were cleaned ultrasonically in acetone and ethanol, in 5 min sequences, and dried in dry $N_2$ gas before being introduced into the chamber.

TABLE 3

Deposition parameters for $Si_xN_y$- and $Si_xN_yC_z$-coatings on silicon wafers.

| Coating | Si-target Power [W] | C-target Power [W] | Temperature [° C.] | Coating thickness [μm] |
|---|---|---|---|---|
| 12 | 1000 | 0 | 250 | 1.2 |
| 13 | 2000 | 0 | 250 | 2.8 |
| 14 | 3000 | 0 | 250 | 4.3 |
| 15 | 4000 | 0 | 250 | 4.4 |
| 16 | 2000 | 0 | 520 | 2.5 |
| 17 | 3000 | 0 | 520 | 3.8 |
| 18* | 4000 | 500 | 250 | 0.50 |
| 19* | 4000 | 700 | 250 | 0.50 |
| 20 | 4000 | 1400 | 250 | 0.55 |
| 21 | 1000 | 700 | 250 | 0.40 |
| 22 | 1000 | 1000 | 250 | 0.85 |
| 23 | 1000 | 1400 | 250 | 0.80 |
| 24* | 4000 | 500 | 520 | 1.10 |
| 25 | 4000 | 700 | 520 | 0.70 |
| 26 | 4000 | 1400 | 520 | 0.70 |
| 27 | 1000 | 700 | 520 | 0.70 |
| 28 | 1000 | 1000 | 520 | 0.70 |

*are also deposited in CoCr-substrate (ASTM F75).

TABLE 4

Parameters held constant for all depositions.

| | |
|---|---|
| Pressure [Pa] | 0.4 |
| Ar flow [sccm] | 360 |
| $N_2$ flow [sccm] | 60 |
| Bias [V] | −100 |
| Pulse freq [hz] | 300 |
| Pulse width [μs] | 200 |
| Substrate | Si-wafer |

The surface roughness (Ra) of the coatings on Si-wafer substrates are around 10 nm, for samples deposited in CoCr-substrates the Ra's are around 20 nm when measured over an area around 0.3 mm². When measured over 1 μm² the surface roughness of the coating on Si-wafers was from 0.3 to 4 nm.

Figure 8A:
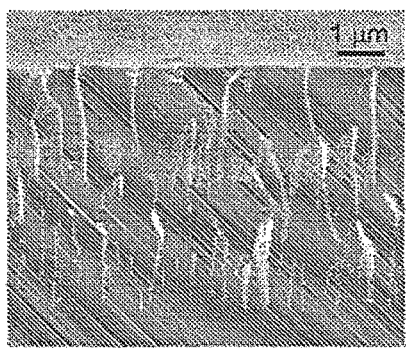
FIGS. 8A-8C show the different structures (FIG. 8A) dense, (FIG. 8B) laminar and (FIG. 8C) columnar materials, respectively, as described in Example 2.
Figure 8B:
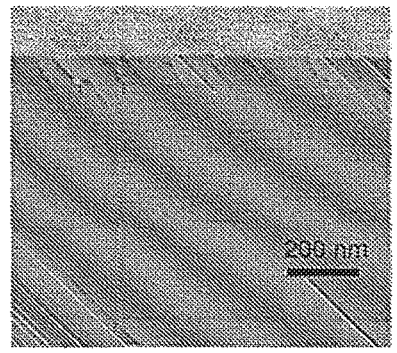
Figure 8C:
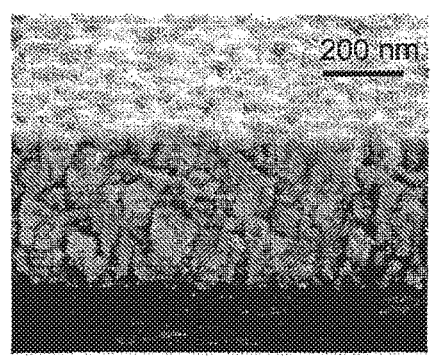

The coatings showed three different types of structure seen in cross-section, dense (coatings Nos. 12-17), laminar (coatings Nos. 18-20 and 24-26) and columnar (coatings Nos. 21-23 and 27-28), see FIGS. 8A-8C.

Hardness measurements were performed as in Example 1, but at a maximum depth of 40 nm. The elastic modulus is determined from these measurements with Poisson's ratios of 0.25 for coatings and the reference material $Si_3N_4$ (Walmsley et al, Poisson's Ratio of Low-Temperature PECVD Silicon Nitride Thin Films, *Journal of Microelectromechanical Systems*, 16 (2007) 622-627), and 0.3 for CoCr were assumed.

The hardness for $Si_xN_yC_z$-coatings ranges from 9 to 19 GPa and $Si_xN_y$-coatings from 17 to 21 GPa. The elastic modulus of the $Si_xN_yC_z$-coatings was from 167 to 212 GPa and $Si_xN_y$-coatings ranges from 148 to 218 GPa, see Table 6.

Figure 9:
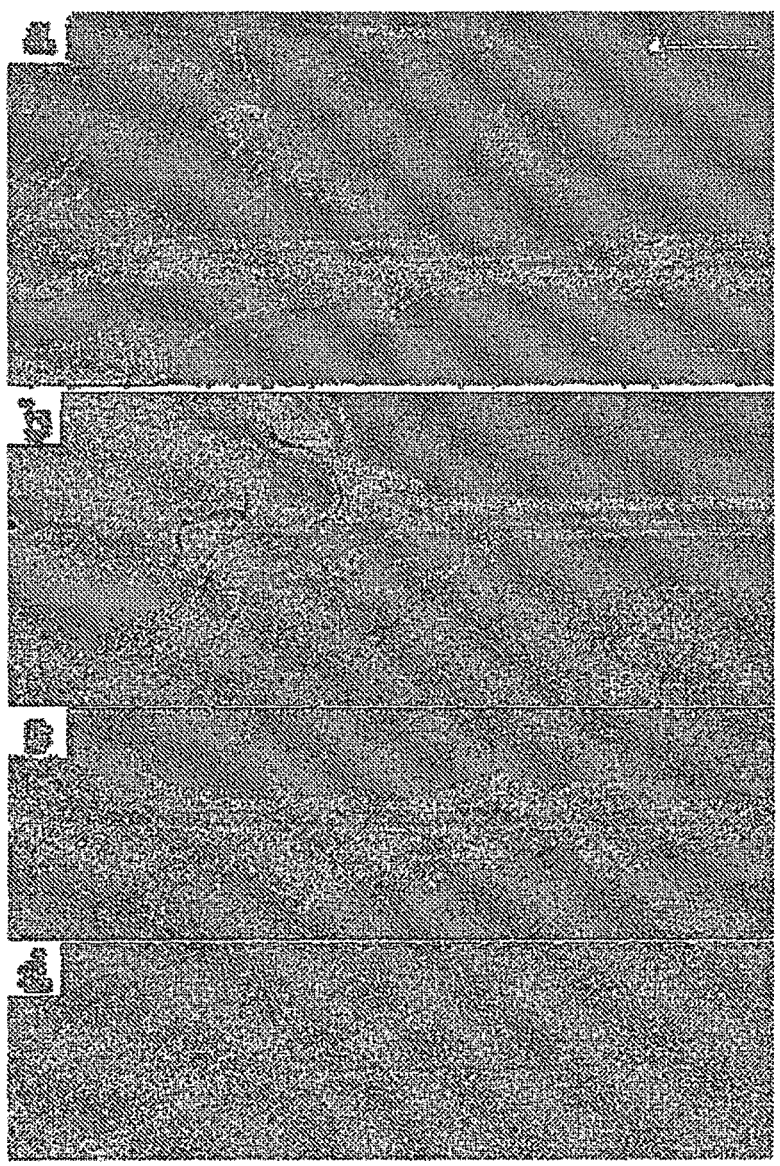
FIG. 9 shows scratches on coatings deposited on silicon wafers for: Panel a) $Si_xN_y$-coating No. 16, b) $Si_xN_y$-coating No. 12, c) $Si_xN_yC_z$-coating No. 20 deposited with a Si-target power of 4 kW, and d) $Si_xN_yC_z$-coating No. 22 deposited at 1 kW, as described in Example 2. The arrow indicates the direction of scratching.

The adhesion and cohesion has been investigated with micro scratching, see FIG. 9. The cohesive failure types for $Si_xN_yC_z$-coatings, cracks and flakes, are believed to be related to different microstructures for coatings deposited at different Si-target powers. When deposited on CoCr, the failure loads was only half of that on Si-wafers. This was expected, due to the softer substrate material and the poor adhesion to CoCr.

Friction and Wear Test

Figure 10:
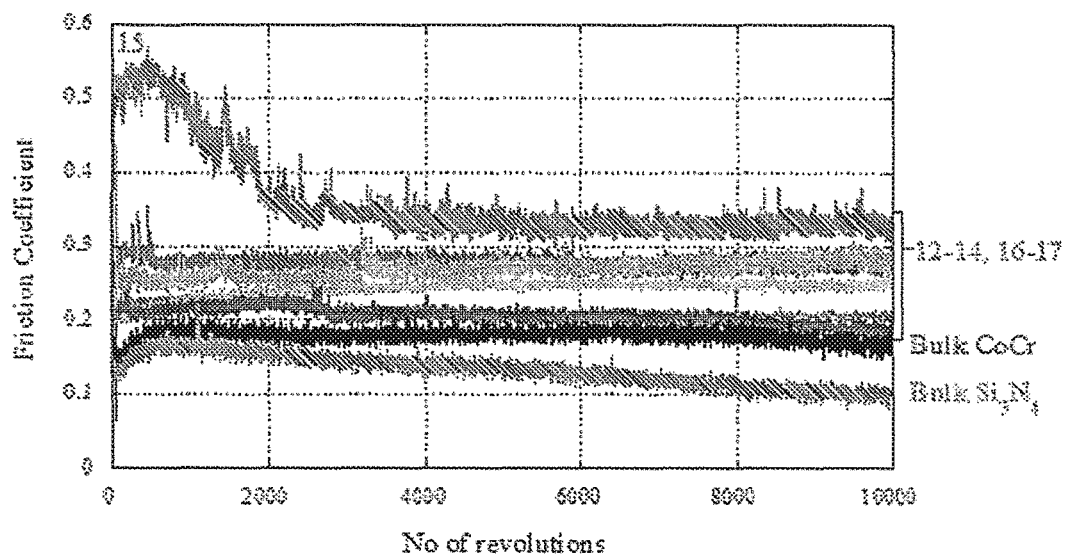
FIG. 10 shows friction coefficient versus number of revolutions from Ball-on-Disc test for tests run for 10,000 cycles, as described in Example 2.

Wear and friction tests were preformed in the same manner with a Ball-on-Disc test as in Example 1. The $Si_xN_y$-coatings tested for 10,000 revolutions has a friction coefficient around 0.20-0.28 (excluding coating No. 15), see FIG. 10. $Si_xN_yC_z$-coatings did not show the same wear resistance and worn through the coating before 1000 revolutions.

Figure 11:
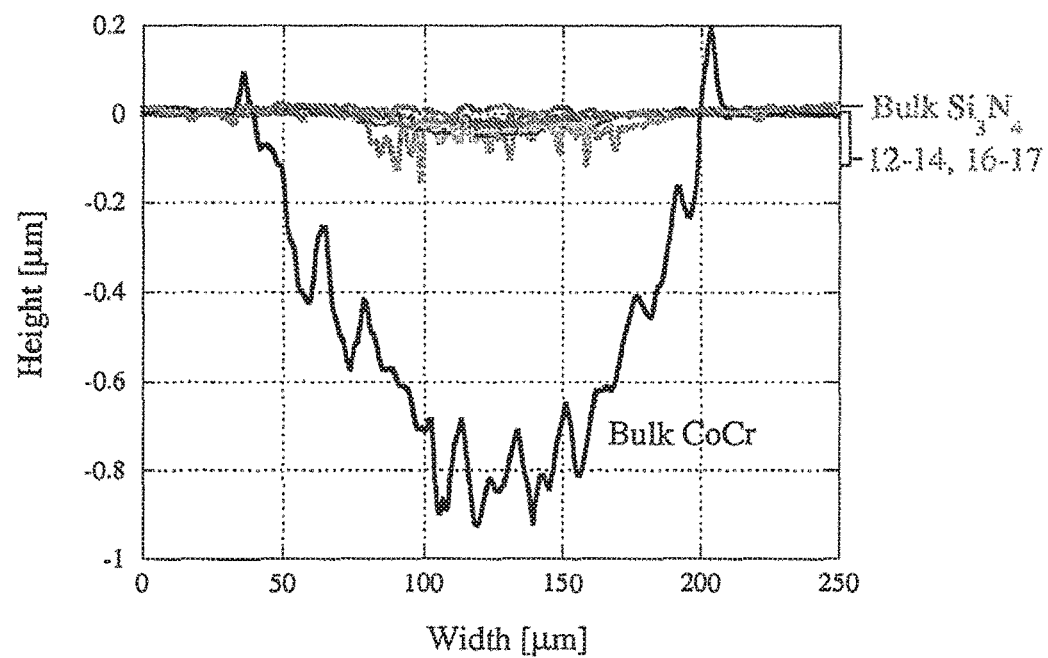
FIG. 11 shows the cross-section of the wear tracks after 10,000 revolutions in ball-on-disc test, as described in Example 2.

The worn cross-sections are displayed in FIG. 11. The calculated specific wear rate is given in Table 6.

Composition

Figure 12A:
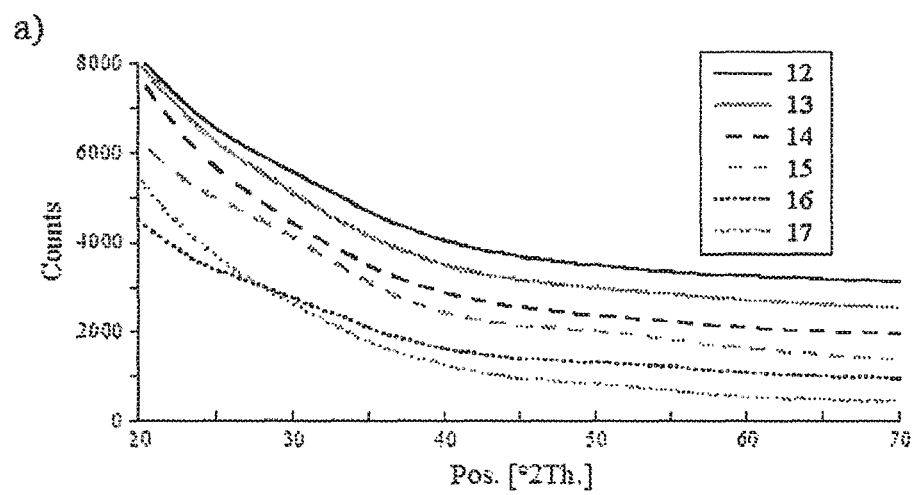
FIGS. 12A and 12B show XRD spectra of FIG. 12A) $Si_xN_y$,— and FIG. 12B) $Si_xN_yC_z$-coatings, respectively, as described in Example 2.
Figure 12B:
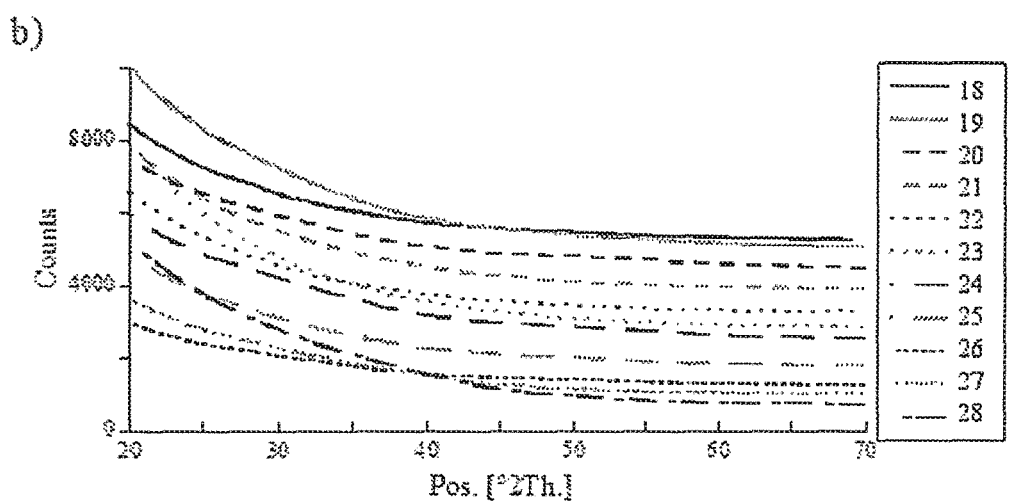
Figure 13A:
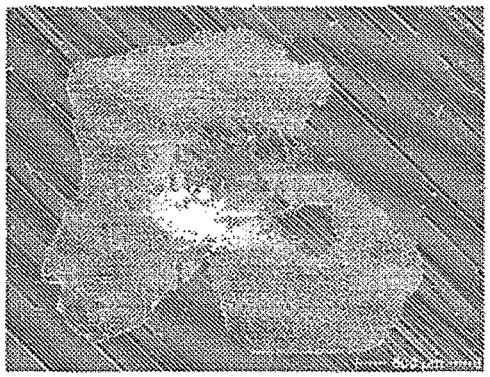
FIGS. 13A-13D show SEM images of coating 12 with additional treatment steps, as described in Example 2: an increased adhesion from FIG. 13A, wherein the standard process has been obtained, to FIG. 13B, introducing an etch process prior deposition, FIG. 13C, with intermittent bias steps, and FIG. 13D, with a nitrogen gradient and high frequency during deposition.
Figure 13B:
Figure 13C:
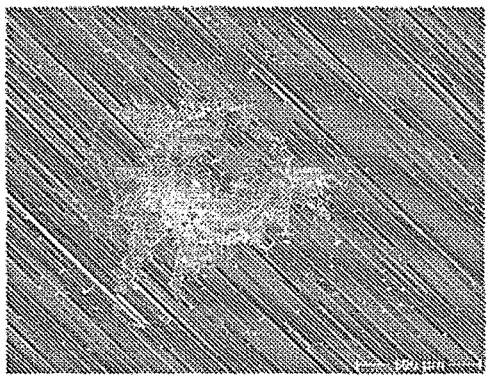
Figure 13D:
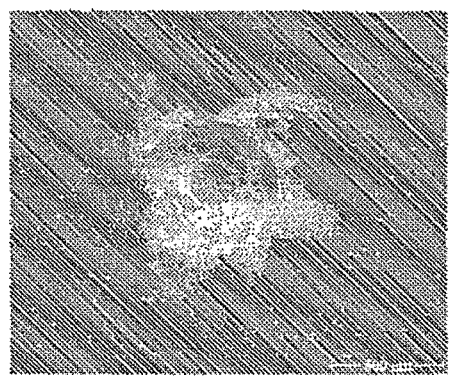

XRD shows no crystalline structure in the coating, only small amorphous bumps could be seen, FIG. 12.

EDS analysis showed the compositions in the coatings, see Table 5. The C content ranges from 0 to 2 at. % without use of the carbon target, and 6 to 35 at. % with the carbon target. The Si was from 37 to 77 at. % and N was from 19 to 29. Note, as above, that the general error when determining compositions using EDS is about ±2 at. %. XPS analysis confirms that the silicon atoms bond to nitrogen atoms.

Summary of the Coating Properties

The coating properties and composition of Example 2 are summarized in Table 5 and 6. The Six Ny-coatings showed similar wear resistance as in Example 1 as well as a slightly lower hardness.

Increased Adhesion

The coatings from Example 2 have been further developed to increase the adhesion with an etch process before the deposition as well as with intermittent bias steps or with a nitrogen gradient and high frequency during the deposition. The processes are described in Tables 7 and 8. The difference in adhesion is shown in FIG. 13 in a Rockwell test with a load of 100 kg.

Other alternatives on improving the adhesion may be made by adhesion layers such as Si or Cr, or a pulsed table as well as targets. Intermittent bias steps and gradients are used to decrease residual stresses and improve the adhesion of the coating.

TABLE 5

Atomic composition for some of the coatings.

| | Atomic ratio (%) | | |
|---|---|---|---|
| Coating | C | Si | N |
| 12 | 1 | 69 | 29 |
| 13 | 2 | 74 | 24 |
| 14 | 1 | 75 | 23 |
| 15 | 0 | 76 | 22 |
| 16 | 1 | 74 | 23 |
| 17 | 1 | 77 | 21 |
| 18 | 6 | 68 | 25 |
| 18* | 8 | 68 | 23 |
| 19 | 9 | 65 | 25 |
| 19* | 9 | 66 | 23 |
| 20 | 14 | 62 | 22 |
| 21 | 23 | 46 | 26 |
| 22 | 30 | 40 | 26 |
| 23 | 35 | 37 | 24 |
| 24 | 6 | 70 | 24 |
| 24* | 8 | 70 | 22 |
| 25 | 9 | 71 | 19 |
| 26 | 15 | 66 | 18 |
| 27 | 22 | 49 | 26 |
| 28 | 29 | 44 | 25 |

Values marked with (*) are tested on CoCr-substrate.

TABLE 7

Etch process for an increase in adhesion.

| | |
|---|---|
| Power Ti-target [W] | 1500 |
| Ar flow [sccm] | 353 |
| Kr flow [sccm] | 267 |
| Etch Bias [V] | −200 |
| Temperature [° C.] | ~325 |
| Duration [s] | 180 |

TABLE 8

Coating processes for increased adhesion.

| Process | Standard | Bias steps | Gradient nitrogen and high frequency |
|---|---|---|---|
| Si-target power [kW] | 1 | 1 | 1 |
| Pressure [Pa] | 0.4 | 0.4 | 0.4 |
| Ar flow [sccm] | 360 | 360 | 360 |
| $N_2$ flow [sccm] | 60 | 60 | 0 to 100, in steps of 1 sccm/60 s, then 60 |
| Bias [V] | −100 | 5 × (−100 for 1400 s, −500 for 200 s) | −100 |

TABLE 6

Mechanical properties of some coatings.

| Coating | Stable μ | Specific wear rate (mm³/Nm) | Mean hardness ± SD (GPa) | Mean elastic modulus ± SD (GPa) | Cohesive failure ± SD (mN) | Adhesive failure ± SD (mn) |
|---|---|---|---|---|---|---|
| 12 | 0.21 | $1.3 \cdot 10^{-7}$ | 21.2 ± 3.1 | 212 18 | — | 214 ± 12 |
| 13 | 0.24 | $2.2 \cdot 10^{-7}$ | 18.4 ± 2.1 | 212 ± 14 | — | 260 ± 15 |
| 14 | 0.28 | $2.3 \cdot 10^{-7}$ | 17.2 ± 3.1 | 199 ± 22 | — | no rupture |
| 15 | >0.33 | $240 \cdot 10^{-7}$ | 17.2 ± 3.0 | 199 ± 30 | — | no rupture |
| 16 | 0.20 | $2.1 \cdot 10^{-7}$ | 18.8 ± 2.6 | 201 ± 12 | — | 265 ± 8 |
| 17 | 0.27 | $4.8 \cdot 10^{-7}$ | 18.8 ± 1.1 | 167 ± 8 | — | no rupture |
| 18 | — | — | 16.0 ± 1.6 | 199 ± 15 | 68 ± 6 | 85 ± 5 |
| 18* | — | n/a | 16.3 ± 2.8 | 216 ± 25 | 26 ± 2 | 36 ± 5 |
| 19 | — | — | 15.2 ± 1.7 | 196 ± 12 | 55 ± 2 | 81 ± 7 |
| 19* | — | n/a | 16.1 ± 2.3 | 202 ± 16 | 20 ± 3 | 33 ± 4 |
| 20 | — | — | 14.8 ± 3.5 | 178 ± 27 | 65 ± 7 | 83 ± 8 |
| 21 | — | — | 10.7 ± 1.4 | 148 ± 12 | 39 ± 6 | 46 ± 3 |
| 22 | — | — | 11.1 ± 1.6 | 149 ± 12 | 42 ± 2 | 52 ± 8 |
| 23 | — | — | 9.9 ± 1.6 | 137 ± 13 | 36 ± 2 | 42 ± 1 |
| 24 | — | — | 18.5 ± 1.6 | 210 ± 10 | 68 ± 6 | 80 ± 4 |
| 24* | — | n/a | 17.0 ± 3.9 | 218 ± 33 | 35 ± 3 | 67 ± 5 |
| 25 | — | — | 18.2 ± 1.6 | 216 ± 11 | 77 ± 3 | 95 ± 5 |
| 26 | — | — | 18.6 ± 2.5 | 202 ± 17 | 68 ± 5 | 86 ± 2 |
| 27 | — | — | 17.5 ± 2.1 | 218 ± 16 | 86 ± 9 | 105 ± 15 |
| 28 | — | — | 15.4 ± 2.6 | 195 ± 18 | 62 ± 4 | 76 ± 2 |
| $Si_3N_4$ | | $1.0 \cdot 10^{-7}$ | 7.4 ± 0.7 | 210 ± 14 | n/a | n/a |
| CoCr | | $60 \cdot 10^{-7}$ | 24.5 ± 4.5 | 314 ± 26 | n/a | n/a |

Values marked with (*) are tested on CoCr-substrate.

TABLE 8-continued

Coating processes for increased adhesion.

| Process | Standard | Bias steps | Gradient nitrogen and high frequency |
|---|---|---|---|
| Pulse freq [hz] | 300 | 300 | 500 |
| Pulse width [μs] | 200 | 200 | 200 |
| Temperature [° C.] | ~325 | ~325 | ~325 |

High Thickness

Figure 14:
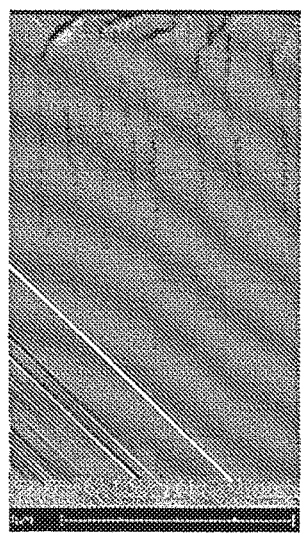
FIG. 14 shows Coating 12 with a thickness of 8 μm, as described in Example 2.

Coatings with high thickness around 10 to 15 μm can be obtained. An example of a thick version of coating 12 is shown in FIG. 14.

Solubility Test

Due to the very low amount of wear particle formation in the tests, it is very difficult to measure the dissolution rate of the actual wear particles using the methods known to the inventors. Instead, a commercial silicon nitride powder (P95H, Akzo Nobel) was mixed with PBS using three different pH values: 4.8, 6.5 and 7.4. PBS has a natural pH of 7.4 and hydrochloric acid was added to decrease the value. The mixture was stored in plastic tubes with plastic lids. The tubes were placed on a rocking platform shaker and stored at 37° C. during 35 and 75 days respectively (Table 9). The average grain size of the powder was approximately 1 μm (measured with SEM and optical microscopy). 100 mg of silicon nitride powder was mixed with 15 ml PBS. After the storage time, the mixture was filtered through a 0.2 μm PTFE membrane using a syringe. Subsequently to the filtration, ICP-MS (Inductively Coupled Plasma Mass Spectrometry) was used to determine the silicon ion content of the solutions.

TABLE 9

Solubility test: number of samples per pH and time point.

| | 100 mg $Si_3N_4$-powder pH | | | PBS without powder | | |
|---|---|---|---|---|---|---|
| Time (days) | 4.8 | 6.5 | 7.4 | 4.8 | 6.5 | 7.4 |
| 35 | 4 | 4 | 4 | 1 | 1 | 1 |
| 75 | 4 | 4 | 4 | 1 | 1 | 1 |

Figure 15:
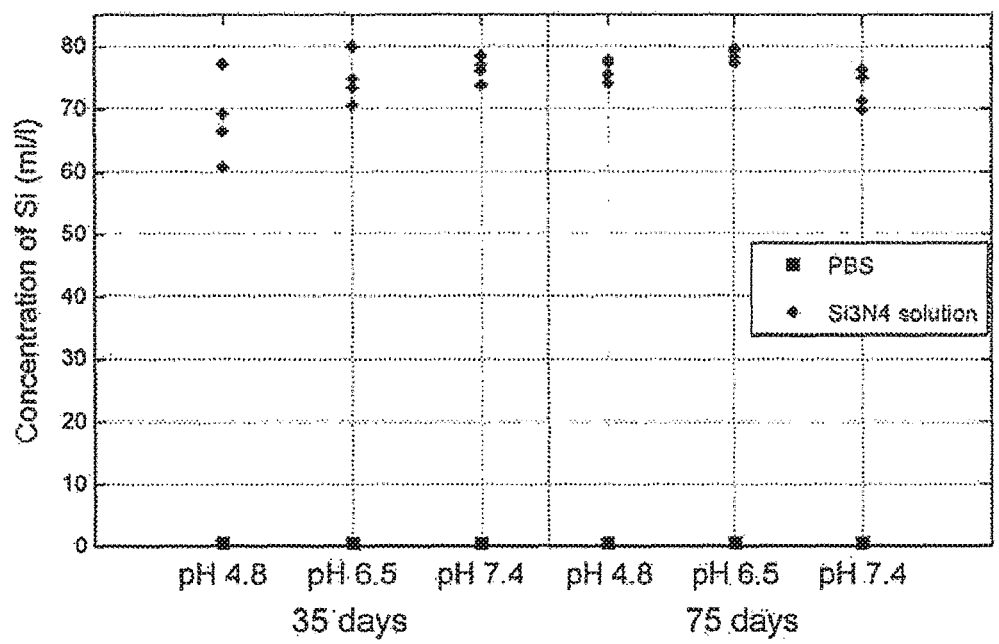
FIG. 15 show the concentration of free Si in PBS solutions of different pH after 35 and 75 days, as described in Example 2.

The concentration of free Si in the filtered solutions indicates that some of the powder has been dissolved. The concentration of Si in the filtered PBS solutions was about 75 ml/l for all pH variations and also approximately the same for the different incubation periods, see FIG. 15. All samples of PBS solutions without any addition of powder showed Si concentrations of less than 0.5 ml/l.

Figure 16:
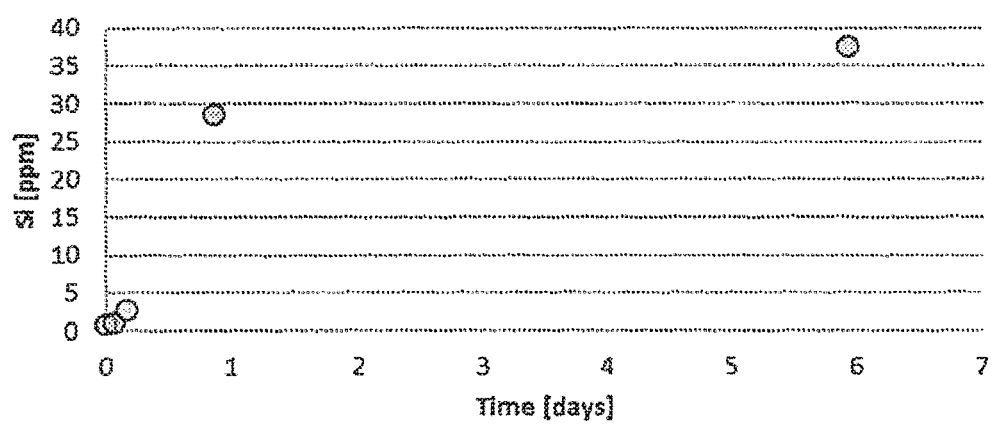
FIG. 16 shows the concentration of silicon in PBS, measured with inductively coupled plasma atomic emission spectroscopy (ICP-AES), as described in Example 2.

Amorphous silicon nitride particles (approx. 30-50 nm) were investigated for exhibiting dissolution also in phosphate buffered saline (PBS, pH ~7.3, 37° C.), FIG. 16. The particles are separated from the PBS by centrifugation.

The tests showed that wear resistant, low friction silicon nitride coatings can be produced at deposition temperatures above about 100° C. The wear resistance was considerably higher than that of CoCr alone and similar to bulk silicon nitride ceramics. In addition, silicon nitride particles were shown to dissolve in simulated body fluids.

The results show that it is feasible to deposit silicon nitride films using sputtering techniques and that the films are more wear resistant than the substrate material. In addition silicon nitride is slowly dissolved in simulated body fluids.

The specific examples and embodiments described herein are exemplary only in nature and are not intended to be limiting of the invention defined by the claims. Further embodiments and examples, and advantages thereof, will be apparent to one of ordinary skill in the art in view of this specification and are within the scope of the claimed invention.

REFERENCES

[1] A. Sargeant and T. Goswami, Hip implants: Paper V. Physiological effects, *Materials & Design* 27 (2006) 287-307.

[2] A. Sargeant and T. Goswami, Hip implants—Paper VI—Ion concentrations, *Materials & Design* 28 (2007) 155-171.

[3] P. Aspenberg, A. Anttila, Y. T. Konttinen, R. Lappalainen, S. B. Goodman, L. Nordsletten, and S. Santavirta, Benign response to particles of diamond and SiC: bone chamber studies of new joint replacement coating materials in rabbits, *Biomaterials* 17 (1996) 807-812.

[4] D. Xiong and S. Ge, Friction and wear properties of UHMWPE/Al2O3 ceramic under different lubricating conditions, *Wear* 250 (2001) 242-245.

[5] B. S. Bal, A. Khandkar, R. Lakshminarayanan, I. Clarke, A. A. Hoffman, and M. N. Rahaman, Fabrication and Testing of Silicon Nitride Bearings in Total Hip Arthroplasty: Winner of the 2007 "HAP" PAUL Award, *The Journal of Arthroplasty* 24 (2009) 110-116.

[6] R. R. Wang, G. E. Welsch, and O. Monteiro, Silicon nitride coating on titanium to enable titanium-ceramic bonding, *Journal of Biomedical Materials Research* 46 (1999) 262-270.

[7] M. Matsuoka, S. Isotani, W. Sucasaire, L. S. Zambom, and K. Ogata, Chemical bonding and composition of silicon nitride films prepared by inductively coupled plasma chemical vapor deposition, *Surface and Coatings Technology* 204 (2010) 2923-2927.

[8] S.-L. Ku and C.-C. Lee, Surface characterization and properties of silicon nitride films prepared by ion-assisted deposition, Surface and Coatings Technology 204 (2010) 3234-3237.

[9] H. P. Löbl and M. Huppertz, Thermal stability of nonstoichiometric silicon nitride films made by reactive dc magnetron sputter deposition, *Thin Solid Films* 317 (1998) 153-156.

[10] K. Kazuo and N. Shinji, Ceramic-coated prosthetic implants, in *Japan Kokai Tokyo Koho*, N.S.P. Co, Editor. 1989: Japan.

[11] L. Huang, K. W. Hipps, J. T. Dickinson, U. Mazur, and X. D. Wang, Structure and composition studies for silicon nitride thin films deposited by single ion bean sputter deposition, *Thin Solid Films* 299 (1997) 104-109.

[12] International Centre for Diffraction Data, Reference files: Cobalt PDF no. 15-0806.

[13] International Centre for Diffraction Data, Reference files: Chromium PDF no. 88-2323.

[14] International Centre for Diffraction Data, Reference files: Cobalt Molybdenum PDF no. 29-0488.

The invention claimed is:

1. An implant comprising a substrate and a wear-resistant coating vapour deposited on a surface of the substrate, the wear-resistant coating comprising silicon nitride and having a thickness of from about 1 micrometer to about 15 micrometer,
   wherein the silicon nitride coating has a composition defined by $Si_xN_yW_z$, where W is C, H and/or O, and 2<x<4, and 3<y<5, and z is such that the coating contains less than 20 atomic percent of C, H and O, wherein the coating has a hardness of from about 5 to about 45 GPa, wherein the coating has a surface roughness (Ra) less than about 20 nm, wherein the coating has a coefficient of friction less than about 0.5.

2. The implant of claim 1, wherein the coating comprises up to about 20 atomic percent of C.

3. The implant of claim 1, wherein the coating comprises a nanocrystalline structure.

4. The implant of claim 1, wherein the coating has a multilayered structure.

5. The implant of claim 1, wherein the coating has a compositional gradient structure.

6. The implant of claim 1, wherein the coating comprises an amorphous structure.

7. The implant of claim 1, wherein the coating has a wear resistance after 10,000 revolutions in bovine serum solution of less than about $10 \times 10^{-7}$ mm$^3$/Nm.

8. The implant of claim 1, wherein the substrate is formed of cobalt-chromium alloy, titanium, titanium alloy, stainless steel, or ceramic.

9. The implant of claim 1, wherein the substrate is formed of ultra high molecular weight polyethylene (UHMWPE).

* * * * *